US008957361B2

(12) United States Patent
Han et al.

(10) Patent No.: US 8,957,361 B2
(45) Date of Patent: Feb. 17, 2015

(54) SWITCHING CIRCUIT, CHARGE SENSE AMPLIFIER INCLUDING SWITCHING CIRCUIT, AND PHOTON COUNTING DEVICE INCLUDING SWITCHING CIRCUIT

(75) Inventors: Sang-wook Han, Busan (KR); Hyun-sik Kim, Daejeon (KR); Young-hun Sung, Hwaseong-si (KR); Jun-hyeok Yang, Daejeon (KR); Gyu-hyeong Cho, Daejeon (KR)

(73) Assignees: Samsung Electronics Co., Ltd., Suwon-si (KR); Korea Advanced Institute of Science and Technology, Daejeon (KR)

( * ) Notice: Subject to any disclaimer, the term of this patent is extended or adjusted under 35 U.S.C. 154(b) by 343 days.

(21) Appl. No.: 13/586,183

(22) Filed: Aug. 15, 2012

(65) Prior Publication Data
US 2013/0161492 A1 Jun. 27, 2013

(30) Foreign Application Priority Data
Dec. 26, 2011 (KR) .................... 10-2011-0142385

(51) Int. Cl.
 H03K 17/00 (2006.01)
 H03M 1/34 (2006.01)
(52) U.S. Cl.
 USPC ........................................ 250/214 A; 341/162
(58) Field of Classification Search
 USPC ............... 250/214 A, 214 SW; 341/155–162; 327/52–57
 See application file for complete search history.

(56) References Cited

U.S. PATENT DOCUMENTS

| 6,188,339 | B1* | 2/2001 | Hasegawa | 341/101 |
| 7,605,571 | B2* | 10/2009 | Kung et al. | 323/223 |
| 8,248,290 | B2* | 8/2012 | Payne | 341/162 |
| 2008/0074092 | A1* | 3/2008 | Kung et al. | 323/271 |
| 2012/0062402 | A1* | 3/2012 | Payne | 341/126 |
| 2013/0021188 | A1* | 1/2013 | Payne | 341/162 |

FOREIGN PATENT DOCUMENTS

| JP | 08-152478 A | 6/1996 |
| JP | 08-211158 A | 8/1996 |
| JP | 09-197053 A | 7/1997 |
| JP | 2000-206255 A | 7/2000 |

* cited by examiner

Primary Examiner — Seung C Sohn
(74) Attorney, Agent, or Firm — NSIP Law

(57) ABSTRACT

A switching circuit, a charge sense amplifier, and a photon counting device are provided. The switching circuit configured to close and open a connection between a first terminal and a second terminal of a predetermined circuit element, includes: a first transistor comprising a source connected to the first terminal, a drain connected to the second terminal, and a gate; a second transistor comprising a drain, a source, and a gate connected to the drain of the second transistor; a current source configured to supply a current flowing through the drain and the source of the second transistor, to generate a gate voltage of the gate of the second transistor; and a multiplexer configured to receive the gate voltage, a reference voltage, and a control signal, and selectively apply the gate voltage or the reference voltage to the gate of the first transistor based on the control signal.

26 Claims, 14 Drawing Sheets

SWITCHING CIRCUIT, CHARGE SENSE AMPLIFIER INCLUDING SWITCHING CIRCUIT, AND PHOTON COUNTING DEVICE INCLUDING SWITCHING CIRCUIT

CROSS-REFERENCE TO RELATED APPLICATION(S)

This application claims the benefit under 35 U.S.C. §119 (a) of Korean Patent Application No. 10-2011-0142385, filed on Dec. 26, 2011, in the Korean Intellectual Property Office, the entire disclosure of which is incorporated herein by reference for all purposes.

BACKGROUND

1. Field

The following disclosure relates to a switching circuit, a charge sense amplifier including the switching circuit, and a photon counting device including the switching circuit.

2. Description of the Related Art

A switch is used to electrically short-circuit or open a connection between two terminals of a circuit element. A charge sense amplifier is an example of a circuit element using a switch. The charge sense amplifier senses a current signal of charges input into an input terminal, and outputs a voltage of which an amplitude is amplified. The charge sense amplifier resets the voltage of an output terminal to an initial value by switching on-off a transistor connected between the input terminal and the output terminal, to sense a new current pulse, after sensing a previous current pulse. During the reset operation of the charge sense amplifier, when the transistor is changed from an on-state to an off-state, charges forming channels of the transistor are discharged to a source and a drain of the transistor, that is, charge injection occurs.

SUMMARY

In one general aspect, there is provided a switching circuit configured to close and open a connection between a first terminal and a second terminal of a predetermined circuit element, including a first transistor including a source connected to the first terminal, a drain connected to the second terminal, and a gate. The switching circuit further includes a second transistor including a drain, a source, and a gate connected to the drain of the second transistor. The switching circuit further includes a current source configured to supply a current flowing through the drain and the source of the second transistor, to generate a gate voltage of the gate of the second transistor. The switching circuit further includes a multiplexer configured to receive the gate voltage, a reference voltage, and a control signal, and selectively apply the gate voltage or the reference voltage to the gate of the first transistor based on the control signal.

The reference voltage is a source voltage of the source of the second transistor.

The first transistor and the second transistor are N-channel field effect transistors (FETs). A source voltage of the source of the second transistor is equal to or greater than a voltage of the first terminal.

The first transistor and the second transistor are P-channel FETs. A source voltage of the source of the second transistor is equal to or less than a voltage of the first terminal.

The first transistor and the second transistor are N-channel FETs. The reference voltage is equal to or less than the voltage of the first terminal.

The first transistor and the second transistor are P-channel FETs. The reference voltage is equal to or greater than the voltage of the first terminal.

The source of the second transistor is connected to the first terminal.

The multiplexer is further configured to apply the gate voltage to the gate of the first transistor when the control signal is in a turn-on state to turn on the first transistor, and apply reference voltage when the control signal is in a turn-off state to turn off the first transistor.

The switching circuit further includes a third transistor including a source connected to the first terminal, a drain connected to the second terminal, and a gate. The switching circuit further includes another multiplexer configured to receive the gate voltage, the reference voltage, and the control signal, and selectively apply the gate voltage or the reference voltage to the gate of the third transistor based on the control signal.

The first transistor and the second transistor are N-channel FETs. The third transistor is an P-channel field effect transistor (FET).

The first transistor and the second transistor are P-channel FETs. The third transistor is an N-channel FET.

The other multiplexer is further configured to apply the reference voltage to the gate of the third transistor when the control signal is in a turn-on state to turn on the first transistor, and apply the gate voltage to the gate of the third transistor when the control signal is in a turn-off state to turn off the first transistor.

The current from the source is a minimum current to turn on the second transistor.

In another general aspect, there is provided a charge sense amplifier including an amplifier including an input terminal and an output terminal, and configured to receive a signal from the input terminal, amplify the signal, and output the amplified signal to the output terminal. The charge sense amplifier further includes a switching circuit configured to reset the amplifier to output an initial-valued signal based on a reset signal. The switching circuit includes a first transistor including a source connected to the input terminal, a drain connected to the output terminal, and a gate. The switching circuit includes a second transistor including a drain, a source, and a gate connected to the drain of the second transistor. The switching circuit includes a current source configured to supply a current flowing through the drain and the source of the second transistor, to generate a gate voltage of the gate of the second transistor. The switching circuit includes a multiplexer configured to receive the gate voltage, a reference voltage, and the reset signal, and selectively apply the gate voltage or the reference voltage to the gate of the first transistor based on the reset signal.

The reference voltage is a source voltage of the source of the second transistor.

The first transistor and the second transistor are N-channel FETs. The reference voltage is equal to or less than a voltage of the input terminal.

The first transistor and the second transistor are P-channel FETs. The reference voltage is equal to or greater than a voltage of the input terminal.

The input terminal includes an inverting input terminal and a non-inverting input terminal. The source of the second transistor is connected to the non-inverting input terminal. The multiplexer is further configured to apply the gate voltage to the gate of the first transistor when the reset signal is in a turn-on state to turn on the first transistor, and apply the reference voltage to the gate of the first transistor when the reset signal is in a turn-off state to turn off the first transistor.

The charge sense amplifier further includes a third transistor including a source connected to the input terminal, a drain connected to the output terminal, and a gate. The charge sense amplifier further includes another multiplexer configured to receive the gate voltage, the reference voltage, and the reset signal, and selectively apply the gate voltage or the reference voltage to the gate of the third transistor based on the reset signal.

The first transistor and the second transistor are N-channel FETs. The third transistor is an P-channel field effect transistor (FET).

The first transistor and the second transistor are P-channel FETs. The third transistor is an N-channel FET.

The other multiplexer is further configured to apply the reference voltage to the gate of the third transistor when the reset signal is in a turn-on state to turn on the first transistor, and apply the gate voltage to the gate of the third transistor when the reset signal is in a turn-off state to turn off the first transistor.

The current source is set to minimize the current.

In still another general aspect, there is provided a photon counting device including a sensor unit including unit sensors configured to detect photons of radioactive rays, and convert the photons into an signal. The photon counting device further includes a read chip including read circuits respectively corresponding to the unit sensors. Each of the read circuits includes an amplifier including an input terminal and an output terminal, and configured to receive the signal from a corresponding one of the unit sensors, amplify the signal, and output the amplified signal to the output terminal. Each of the read circuits further includes a switching circuit configured to reset the amplifier to output an initial-valued signal based on a reset signal. Each of the read circuits further includes a comparer configured to compare a voltage of the output terminal with a predetermined threshold value, and output a result of the comparison. Each of the read circuits further includes a signal processor configured to receive the result of the comparison from the comparer, and transmit the reset signal to the switching circuit and a digital signal based on the result of the comparison. Each of the read circuits further includes a counter configured to receive the digital signal from the signal processor, and count a number of photons based on the digital signal. The switching circuit includes a first transistor including a source connected to the input terminal, a drain connected to the output terminal, and a gate. The switching circuit further includes a second transistor including a drain, a source, and a gate connected to the drain of the second transistor. The switching circuit further includes a current source configured to supply a current flowing through the drain and the source of the second transistor, to generate a gate voltage of the gate of the second transistor. The switching circuit further includes a multiplexer configured to receive the gate voltage, a reference voltage, and the reset signal, and selectively apply the gate voltage or the reference voltage to the gate of the first transistor based on the reset signal.

The source of the second transistor is connected to the input terminal. The reference voltage is a source voltage of the source of the second transistor. The multiplexer is further configured to apply the gate voltage to the gate of the first transistor when the reset signal is in a turn-on state to turn on the first transistor, and apply the reference voltage to the gate of the first transistor when the reset signal is in a turn-off state to turn off the first transistor.

In yet another general aspect, there is provided an apparatus including a circuit element including a first terminal and a second terminal. The apparatus further includes a first transistor configured to close and open a connection between the first terminal and the second terminal. The apparatus further includes a second transistor comprising a drain connected to a current source, a source, and a gate connected to the drain of the second transistor, the second transistor configured to generate a voltage of the gate and a voltage of the source. The apparatus further includes a multiplexer configured to receive the voltage of the gate, the voltage of the source, and a control signal, and turn on and off the first transistor based on the voltage of the gate, the voltage of the source, and the control signal, to close and open the connection.

Other features and aspects may be apparent from the following detailed description, the drawings, and the claims.

Figure 1A:
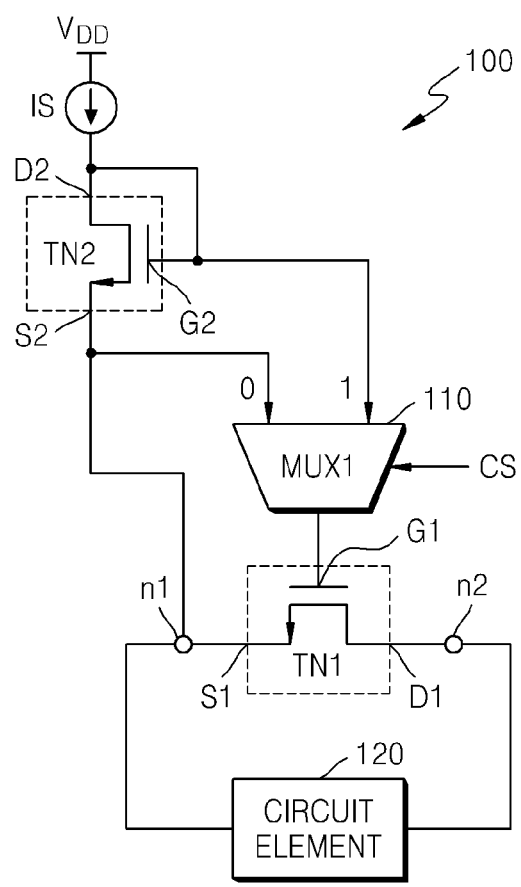
FIGS. 1A through 1D are structural diagrams illustrating examples of switching circuits.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

It is understood that the features of the disclosure may be embodied in different forms and should not be constructed as limited to the examples set forth herein. Rather, examples are provided so that this disclosure will be thorough and complete, and will convey the full scope of the disclosure to those skilled in the art. The drawings may not be necessarily to scale, and, in examples, proportions may have been exaggerated in order to clearly illustrate features of the examples.

FIGS. 1A through 1D are structural diagrams illustrating examples of switching circuits. Referring to FIG. 1A, a switching circuit 100 resets a voltage of an output terminal of a circuit element 120 to an initial value based on a control signal CS. The switching circuit 100 includes a first transistor TN1, a second transistor TN2, and a multiplexer 110. The first transistor TN1 is an N-channel field effect transistor (FET) or an N-channel metal-oxide-semiconductor FET (MOSFET) including a source S1 connected to a first terminal n1 of the circuit element 120, and a drain D1 connected to a second terminal n2 of the circuit element 120. The first transistor TN1 is turned on and off based on a voltage applied to the gate G1, and performs a switching operation to open and close a connection between the first terminal n1 and the second terminal n2. That is, the first transistor TN1 is turned on and off based on the control signal CS, to reset the circuit element 120.

Examples of the circuit element 120 may include, but are not limited to, a capacitor, a resister, a condenser, a coil, a diode, a transformer, and/or an amplifier. In addition, the circuit element 120 may not have to include a single element and may include a combination of various elements.

During a reset operation, the switching circuit 100 adjusts the voltage applied to the gate G1 of the first transistor TN1 by using the second transistor TN2 and the multiplexer 110 to perform the switching operation of the first transistor TN1 while minimizing a gate-to-source voltage $V_{GS,1}$ of the first transistor TN1. The second transistor TN2 is an N-channel FET or an N-channel MOSFET connected to a current source IS supplying a current to a drain D2 and a source S2 of the second transistor TN2. For example, the current source IS may be a variable resistor. However, the current source IS is not limited to a variable resistor, and may be any current source. A gate G2 of the second transistor TN2 is connected to the drain D2 such that a voltage $V_{DD}$ to operate the second transistor TN2 is applied to the gate G2. Based on a flow of a current $I_{DS,2}$ between the drain D2 and the source S2 of the second transistor TN2, a gate-to-source voltage $V_{GS,2}$ of the second transistor TN2 is formed.

The multiplexer 110 receives a source voltage $V_{S2}$ (e.g., about 0 V) and a gate voltage $V_{G2}$ (e.g., about 5 V or the voltage $V_{DD}$), of the second transistor TN2, via a first input terminal and a second input terminal, respectively. When the multiplexer 110 applies the gate voltage $V_{G2}$ (e.g., an input 1) to the gate G1 of the first transistor TN1, the gate-to-source voltage $V_{GS,1}$ of the first transistor TN1 is equal to or greater than the gate-to-source voltage $V_{GS,2}$ of the second transistor TN2. Thus, the first transistor TN1 is turned on. When the multiplexer 110 applies the source voltage $V_{S2}$ (e.g., an input 0) to the gate G1 of the first transistor TN1, the gate-to-source voltage $V_{GS,1}$ is equal to or less than a threshold voltage $V_{TH1}$ (e.g., about 0.5 V) of the first transistor TN1. Thus, the first transistor TN1 is turned off.

The multiplexer 110 selects and outputs the gate voltage $V_{G2}$ or the source voltage $V_{S2}$, of the second transistor TN2, based on a value of the control signal CS. For example, if the value of the control signal CS is about 5 V, the multiplexer 110 selects and outputs the gate voltage $V_{G2}$. If the value of the control signal CS is, for example, about 0 V, the multiplexer 110 selects and outputs the source voltage $V_{S2}$. The first transistor TN1 is switched on-off based on the output of the multiplexer 110.

Figure 1B:
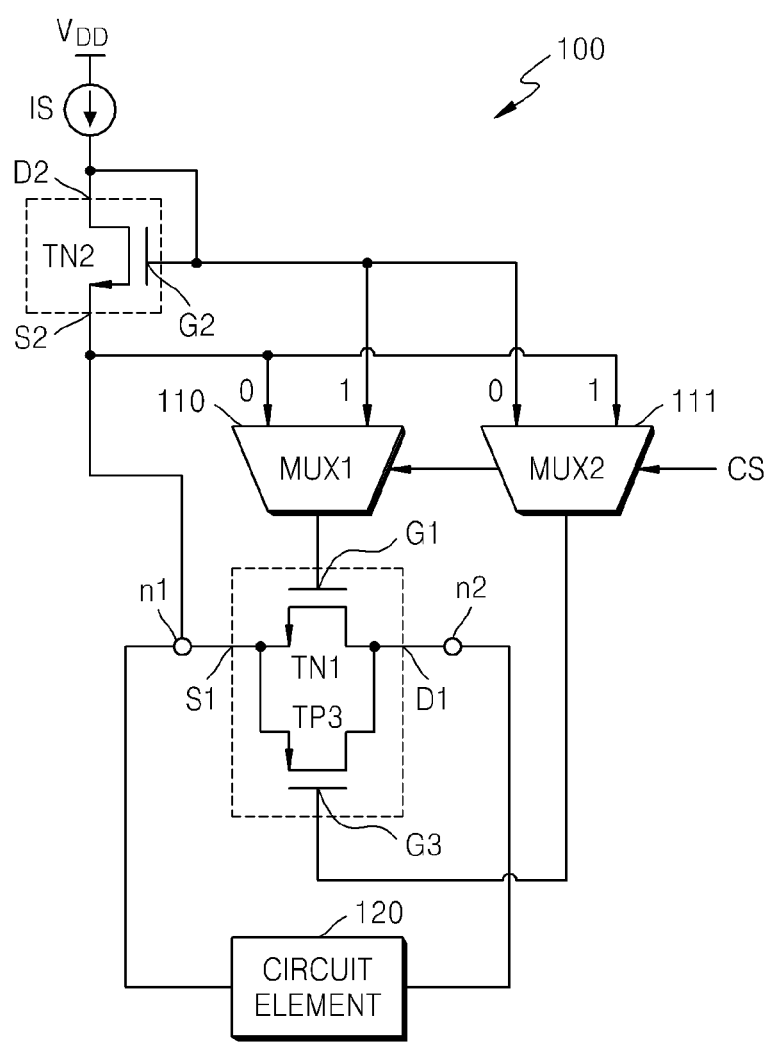

Referring to FIG. 1B, the switching circuit 100 further includes a third transistor TP3 and a multiplexer 111. The third transistor TP3 is an P-channel FET or an P-channel MOSFET. The first transistor TN1 and the third transistor TP3 are connected in parallel to each other. The multiplexer 111 selects and outputs a voltage to be applied to a gate G3 of the third transistor TP3 based on the value of the control signal CS. The third transistor TP3 compensates for a negative channel charge generated from the first transistor TN1.

For example, when the control signal CS is in a turn-on state to turn on the first transistor TN1 (for example, when the value of the control signal CS is about 5 V), and the control signal CS is input into the multiplexer 111, the multiplexer 111 selects and outputs an input 1 corresponding to the source voltage $V_{S2}$ of the second transistor TN2. Thus, the source voltage $V_{S2}$ of the second transistor TN2 is input into the gate G3 of the third transistor TP3. When the control signal CS is in a turn-off state to turn off the first transistor TN1 (for example, when the value of the control signal CS is about 0 V), and the control signal CS is input into the multiplexer 111, the multiplexer 111 selects and outputs an input 0 corresponding to the gate voltage $V_{G2}$ of the second transistor TN2. Thus, the gate voltage $V_{G2}$ of the second transistor TN2 is input into the gate G3 of the third transistor TP3.

Figure 1C:
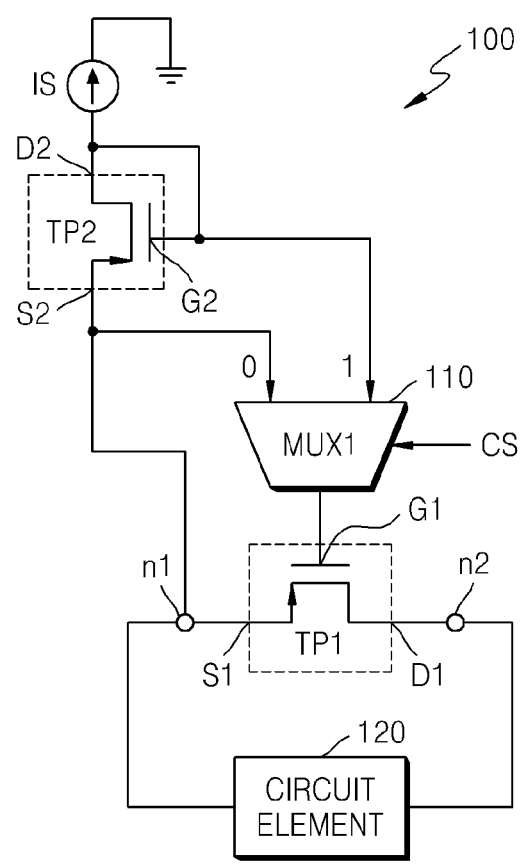

Referring to FIG. 1C, the switching circuit 100 includes a first transistor TP1 and a second transistor TP2 that are P-channel FETs or P-channel MOSFETs. With regard to the second transistor TP2, a current flows from a source S2 to a drain D2 by a current source IS connected to ground. A gate-to-source voltage $V_{GS,2}$ is formed in the second transistor TP2 based on the current between the source S2 and the drain D2 of the second transistor TP2.

When the value of the control signal CS is, for example, about 5 V, the multiplexer 110 selects and outputs an input 1 corresponding to a gate voltage $V_{G2}$ of a gate G2 of the second transistor TP2. When the value of the control signal CS is, for example, about 0 V, the multiplexer 110 selects and outputs an input 0 corresponding to a source voltage $V_{S2}$ of the second transistor TP2. The first transistor TP1 receives the output of the multiplexer 110 via a gate G1 so as to be switched on-off.

Since a source voltage $V_{S1}$ of the first transistor TP1 and the source voltage $V_{S2}$ of the second transistor TP2 are the same, when the gate voltage $V_{G2}$ of the second transistor TP2 is applied to the gate G1 of the first transistor TP1, the first transistor TP1 and the second transistor TP2 operate as a current mirror. Thus, when the gate voltage $V_{G2}$ of the second transistor TP2 is applied to the gate G1 of the first transistor TP1, the same current as the current flowing in the second transistor TP2 flows in the first transistor TP1. In addition, the gate-to-source voltage $V_{GS,2}$ of the second transistor TP2 is the same as a gate-to-source voltage $V_{GS,1}$ of the first transistor TP1, because of the current flowing in the second transistor TP2. Thus, the first transistor TP1 is turned on.

The current source IS is set to minimize an amount of the current flowing in the second transistor TP2. Accordingly, a relatively small amount of current also flows in the first transistor TP1 when the gate voltage $V_{G2}$ of the second transistor TP2 is applied to the gate G1 of the first transistor TP1. Thus, an amount of the gate-to-source voltage $V_{GS,1}$ of the first transistor TP1 is reduced, and an amount of charge injection charges of the first transistor TP1 is reduced. In addition, when the source voltage $V_{S2}$ of the second transistor TP2 is input into the gate G1 of the first transistor TP1, the gate-to-source voltage $V_{GS,1}$ of the first transistor TP1 is about 0 V that is greater than a threshold voltage (for example, about −0.5 V) of the first transistor TP1. Thus, the first transistor TP1 is turned off.

Figure 1D:
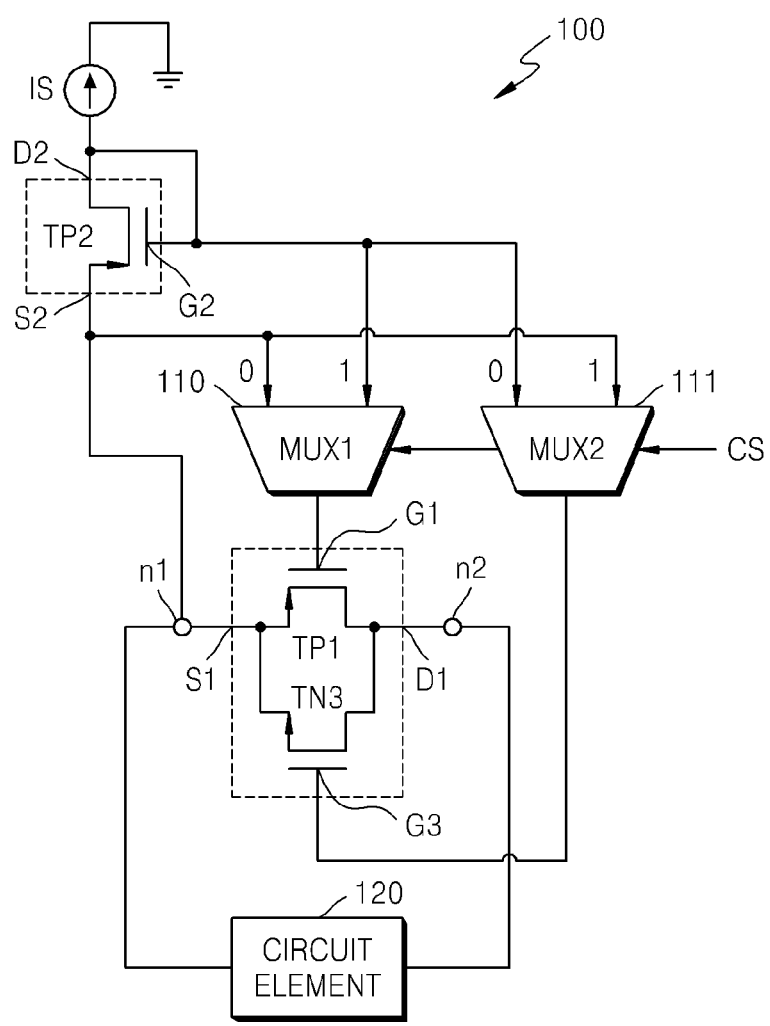

Referring to FIG. 1D, the switching circuit 100 further includes a third transistor TN3 and the multiplexer 111. The third transistor TN3 is an N-channel FET or an N-channel MOSFET. The first transistor TP1 and the third transistor TN3 are connected in parallel to each other. The multiplexer 111 selects and outputs a voltage to be applied to a gate G3 of the third transistor TN3 based on the control signal CS. The third transistor TN3 compensates for a positive channel charge generated from the first transistor TP1.

For example, when the control signal CS is in a turn-on state to turn on the first transistor TP1, and the control signal CS is input into the multiplexer 111, the multiplexer 111 selects and outputs an input 1 corresponding to the source voltage $V_{S2}$ of the second transistor TP2. Thus, the source voltage $V_{S2}$ of the second transistor TP2 is applied to the gate G3 of the third transistor TN3. When the control signal CS is in a turn-off state to turn off the first transistor TP1, and the control signal CS is input into the multiplexer 111, the multiplexer 111 selects and outputs an input 0 corresponding to the gate voltage $V_{G2}$ of the second transistor TP2. Thus, the gate voltage $V_{G2}$ is input into the gate G3 of the third transistor TN3.

Figure 2:
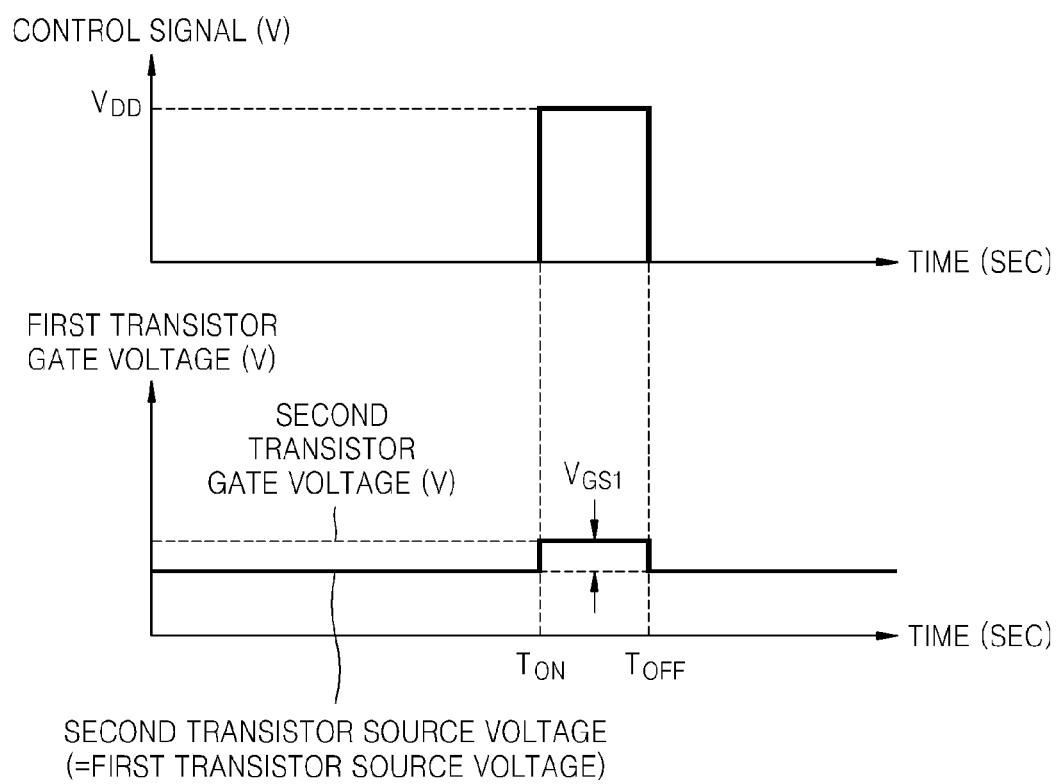
FIG. 2 is a graph illustrating examples of waveforms of a control signal and a gate voltage of a first transistor, of the switching circuit of FIG. 1A.

FIG. 2 is a graph illustrating examples of waveforms of a control signal and the gate voltage of the first transistor TN1, of the switching circuit of FIG. 1A. For a period of time 0 to $T_{ON}$, the control signal input into the multiplexer 110 is 0 V, and a source voltage of the second transistor TN2 is applied to the gate G1 of the first transistor TN1. In this case, since a gate-to-source voltage of the first transistor TN1 is 0 V that is smaller than a threshold value (e.g., 0.5 V) of the first transistor TN1, the first transistor TN1 is turned off.

For a period of time $T_{ON}$ to $T_{OFF}$, the control signal input into the multiplexer 110 is $V_{DD}$, and a gate voltage of the second transistor TN2 is applied to the gate G1 of the first transistor TN1. In this case, the first transistor TN1 and the second transistor TN2 operate as a current mirror, and the gate-to-source voltage $V_{GS,1}$ of the first transistor TN1 is the same as a gate-to-source voltage of the second transistor TN2. A current flowing in the first transistor TN1 is determined based on a current flowing in the second transistor TN2. Thus, when the gate voltage of the second transistor TN2 is applied to the gate G1 of the first transistor TN1, even if an amplitude of the gate-to-source voltage $V_{GS,1}$ of the first transistor TN1 is not relatively high, the first transistor TN1 is turned on.

The second transistor TN2 has the same channel width and the same channel length as a channel width $W_1$ and a channel length $L_1$ of the first transistor TN1. When the gate voltage of the second transistor TN2 is applied to the gate G1 of the first transistor TN1, an amount of current flowing in the second transistor TN2 is the same as an amount of current flowing in the first transistor TN1. When the amount of the current flowing in the second transistor TN2 is adjusted by using the current source IS, the amount of the current flowing in the first transistor TN1 is correspondingly adjusted. Thus, the switching circuit 100 minimizes the gate-to-source voltage $V_{GS,1}$ of the first transistor TN1 as long as a stable on-off switching operation is performed. Accordingly, during the switching operation of the first transistor TN1, an amount of charge injection charges discharged from the first transistor TN1 is reduced.

Figure 3:
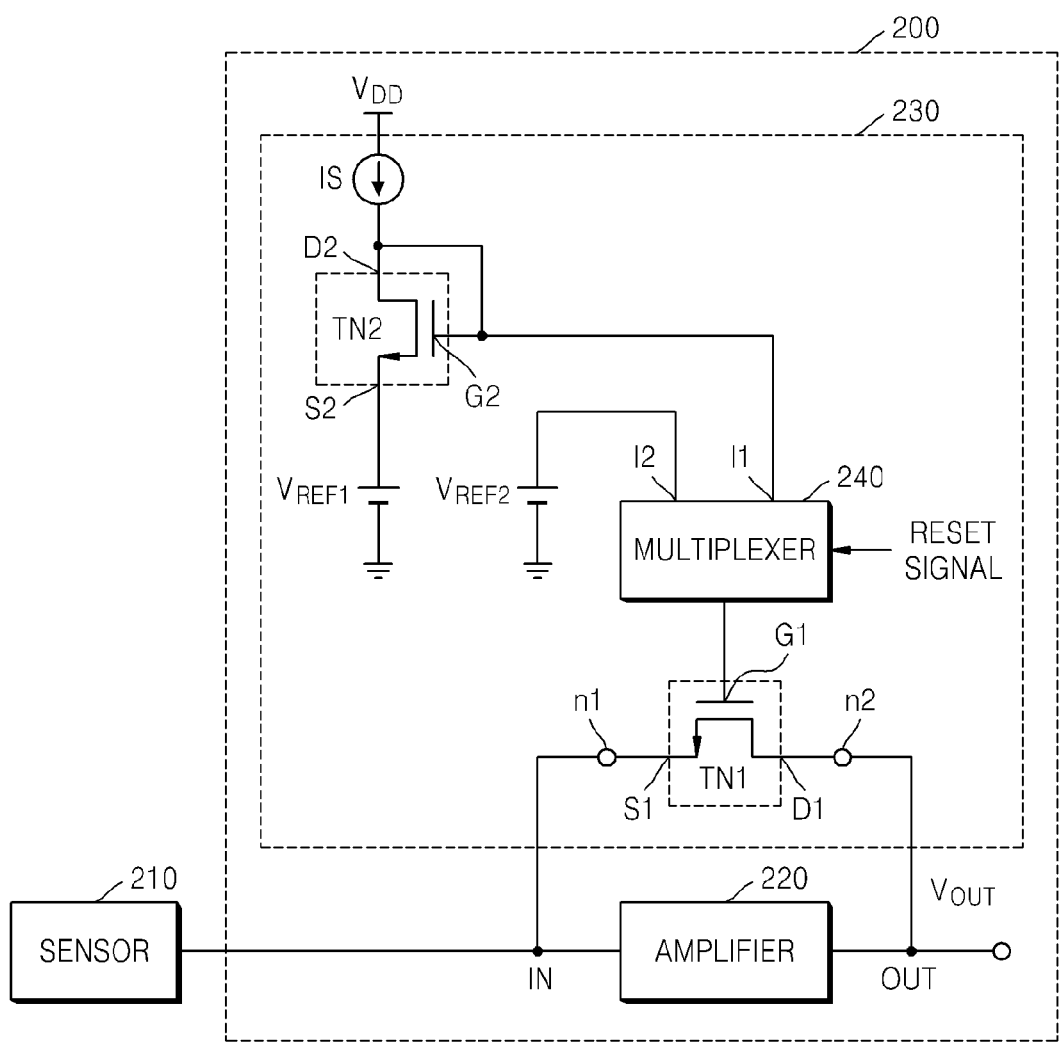
FIG. 3 is a structural diagram illustrating an example of a charge sense amplifier.

FIG. 3 is a structural diagram illustrating an example of a charge sense amplifier 200. The charge sense amplifier 200 senses a current signal in a semiconductor integrated circuit, amplifies an amplitude of the current signal, and outputs a voltage based on the current signal through an output terminal. The charge sense amplifier 200 includes an amplifier 220 and a switching circuit 230. The amplifier 220 receives and amplifies a current signal from an input terminal IN, which is generated by a sensor 210. The amplifier 220 outputs a voltage $V_{OUT}$ based on the current signal through an output terminal OUT. The switching circuit 230 resets the voltage $V_{OUT}$ to an initial value. The sensor 210 senses photons included in, for example, radioactive rays, and generates a pulse current (e.g., the current signal) based on the sensed photons. The sensor 210 may include, but is not limited to, a photoconductor configured to receive X-rays and generate a current based on the X-rays, and/or a photodiode.

The switching circuit 230 resets the voltage $V_{OUT}$ of the output terminal OUT of the amplifier 220 to the initial value based on a reset signal RESET SIGNAL. The switching circuit 230 includes a first transistor TN1, a second transistor TN2, and a multiplexer 240. The first transistor TN1 is an N-channel FET or an N-channel MOSFET including a source 51 connected to the input terminal IN (or a first terminal n1) of the amplifier 220, and a drain D1 connected to the output terminal OUT (or a second terminal n2) of the amplifier 220. The first transistor TN1 is switched on and off based on the reset signal RESET SIGNAL, to reset the amplifier 220.

In more detail, when a voltage is applied to a gate of an N-channel FET, a channel is formed between a drain and a source of the N-channel FET. An amount of charges forming a channel of an FET may be represented according to Equation 1 below.

$$Q_{Channel}=C_{ox}WL(V_{DD}-V_{REF}-V_{TH}) \quad (1)$$

In this example, $Q_{channel}$ is the amount (C) of charges forming the FET, $C_{ox}$ is a gate oxide capacitance per unit area (F/m²) of the FET, W is a channel width (m) of the FET, L is a channel length (m) of the FET, $V_{DD}$ is a gate voltage (V) of the FET, $V_{REF}$ is a source voltage (V) of the FET, and $V_{TH}$ is a threshold voltage (V) of the FET.

Regarding the N-channel FET, when a gate-to-source voltage $V_{GS}$ is greater than a threshold voltage $V_{TH}$, the N-channel FET is turned on. When the gate to source voltage $V_{GS}$ is equal to or less than the threshold voltage $V_{TH}$, the N-channel FET is turned off. In this example, a gate-to-source voltage $V_{GS}$ of a FET is a voltage obtained by subtracting a source voltage from a gate voltage of the FET. The threshold voltage $V_{TH}$ of the FET is a minimum amount of gate-to-source voltage $V_{GS}$ of the FET, at which a conduction channel begins to be formed between a drain and a source of the FET such that a current flows in proportion to a drain-to-source voltage $V_{DS}$ of the FET.

When the FET is changed from an on-state to an off-state, charges (hereinafter, referred to as "channel charges") forming channels of the FET are discharged to the drain and the source of the FET, which is referred to as charge injection. As an amount of the channel charges is increased, the charge injection further occurs. In addition, the charge injection may unexpectedly affect peripheral circuit elements. For example, due to the charge injection, an offset voltage may be formed in the input terminal IN of the amplifier 220, may be amplified by the amplifier 220, thereby causing noise in the output terminal OUT. To prevent the charge injection, a voltage applied to the gate of the FET needs to be reduced. However, there is a limit in reducing the voltage applied to the gate to ensure a turn-on operation TURN ON of the FET. In addition, since the threshold voltage $V_{TH}$ of the FET varies based on a temperature, it is difficult to determine the gate voltage to turn on the FET as any one value.

In examples, during a reset operation RESET, the charge sense amplifier 200 adjusts a voltage applied to a gate G1 of the first transistor TN1 by using the second transistor TN2 and the multiplexer 240 to perform a switching operation of the first transistor TN1 while minimizing an amount of a gate-to-source voltage $V_{GS,1}$ of the first transistor TN1. The second transistor TN2 is an N-channel FET or an N-channel MOSFET connected to a current source IS supplying a current to a drain D2 and a source S2 of the second transistor TN2. For example, the current source IS may be a variable resistor. However, the current source IS is not limited to a variable resistor, and may be any current source. A gate G2 of the second transistor TN2 is connected to the drain D2 such that a voltage $V_{DD}$ to operate the second transistor TN2 is applied to the gate G2. Based on a flow of a current $I_{DS,2}$ between the drain D2 and the source S2 of the second transistor TN2, a gate-to-source voltage $V_{GS,2}$ of the second transistor TN2 is formed.

Since the first transistor TN1 is the N-channel FET, a reference voltage $V_{REF1}$ that is equal to or greater than a voltage of the input terminal IN of the amplifier 220 may be applied to the source S2 of the second transistor TN2. In another example, if the first transistor TN1 is an P-channel FET or an P-channel MOSFET, the reference voltage $V_{REF1}$ is equal to or less than the voltage of the input terminal IN of the amplifier 220. As shown in FIG. 3, the reference voltage $V_{REF1}$ is formed by an independent voltage source connected to ground. In another example, as descried later with reference to FIG. 4A, the reference voltage $V_{REF1}$ may be a voltage of an input terminal IN2 of the amplifier 220, as the source S2 of the second transistor TN2 is connected to the input terminal IN2 of the amplifier 220.

The multiplexer 240 receives a gate voltage $V_{G2}$ of the second transistor TN2 via a first input terminal I1, and receives a reference voltage $V_{REF2}$ via a second input terminal I2. The reference voltage $V_{REF2}$ is determined based on the voltage of the input terminal IN of the amplifier 220. Since the first transistor TN1 is the N-channel FET, the reference voltage $V_{REF2}$ is equal to or less than the voltage of the input terminal IN of the amplifier 220. In another example, if the first transistor TN1 is the P-channel FET or the P-channel MOSFET, the reference voltage $V_{REF2}$ is equal to or greater than the voltage of the input terminal IN of the amplifier 220. As shown in FIG. 3, the reference voltage $V_{REF2}$ is formed by an independent voltage source connected to ground. In another example, as described later with reference to FIG. 4A, the reference voltage $V_{REF2}$ may be the same reference voltage as any one of input terminals of a multiplexer 240 and the input terminal IN of the amplifier 220.

When the multiplexer 240 applies the gate voltage $V_{G2}$ (e.g., the voltage $V_{DD}$) of the second transistor TN2 to the gate G1 of the first transistor TN1, the gate-to-source voltage $V_{GS,1}$ of the first transistor TN1 is equal to or greater than the gate-to-source voltage $V_{GS,2}$ of the second transistor TN2. Thus, the first transistor TN1 is turned on. When the multiplexer applies the reference voltage $V_{REF2}$ (e.g., about 0 V) to the gate G1 of the first transistor TN1, the gate-to-source voltage $V_{GS,1}$ of the first transistor TN1 is about 0 V, and is equal to or less than a threshold voltage $V_{TH,1}$ (e.g., about 0.5 V) of the first transistor TN1. Thus, the first transistor TN1 is turned off.

The multiplexer 240 selects and outputs the gate voltage $V_{G2}$ of the second transistor TN2 or the reference voltage $V_{REF2}$ based on a value of the reset signal RESET SIGNAL. For example, if the value of the reset signal RESET SIGNAL is 5 V, the multiplexer 240 selects and outputs the gate voltage $V_{G2}$ of the second transistor TN2. If the value of the reset signal RESET SIGNAL is, for example, 0 V, the multiplexer 240 selects and outputs the reference voltage $V_{REF2}$. The first transistor TN1 is switched on-off based on the output of the multiplexer 240.

An amount of charges forming the channel of the first transistor TN1 may be represented according to Equation 2 below.

$$Q_{Channel} = C_{ox,1} W_1 L_1 (V_{GS,1} - V_{TH,1}) \quad (2)$$

In this example, $Q_{channel}$ is the amount (C) of charges forming the first transistor TN1, $C_{ox,1}$ is a gate oxide capacitance per unit area (F/m²) of the first transistor TN1, $W_1$ is a channel width (m) of the first transistor TN1, $L_1$ is a channel length (m) of the first transistor TN1, $V_{GS,1}$ is the gate-to-source voltage (V) of the first transistor TN1, and $V_{TH,1}$ is the threshold voltage (V) of the first transistor TN1.

Since a drain voltage $V_{D2}$ and the gate voltage $V_{G2}$, of the second transistor TN2, are the same, the second transistor TN2 operates in saturation region. Thus, a relationship between a current $I_D$ flowing below the drain D2 and the source S2 of the second transistor TN2 and the gate-to-source voltage $V_{GS,2}$ of the second transistor TN2 may be represented as Equation 3 below.

$$I_D = \frac{1}{2}(\mu_n C_{ox,2})\left(\frac{W_2}{L_2}\right)(V_{GS,2} - V_{TH,2})^2 \quad (3)$$

In this example, $I_D$ is the current (A) flowing between the drain D2 and the source S2 of the second transistor TN2, $\mu_n$ is a mobility (m²/Vs) of electrons, $C_{ox,2}$ is a gate oxide capacitance per unit area (F/m²) of the second transistor TN2, $W_2$ is a channel width (m) of the second transistor TN2, $L_2$ is a channel length (m) of the second transistor TN2, $V_{GS,2}$ is the gate-to-source voltage (V) of the second transistor TN2, and $V_{TH,2}$ is a threshold voltage (V) of the second transistor TN2.

According to Equation 3 above, if the current $I_D$ flowing in the second transistor TN2 is reduced, the gate-to-source voltage $V_{GS,2}$ of the second transistor TN2 is reduced. Also, if the current $I_D$ flowing in the second transistor TN2 is reduced, the gate-to-source voltage $V_{GS,1}$ of the first transistor TN1 is reduced because the multiplexer 240 applies the gate voltage $V_{G2}$ of the second transistor TN2 to the gate G1 of the first transistor TN1. Therefore, the amount of charges forming the first transistor TN1 is reduced according to Equation 2 above.

By minimizing an amount of the current $I_D$ flowing in the second transistor TN2 while the second transistor TN2 is turned on, an amount of the gate-to-source voltage $V_{GS,2}$ of the second transistor TN2 is minimized. If the current source IS is a variable resistor, a variance of the current $I_D$ in the second transistor TN2 is proportional to a value of the variable resistor. Accordingly, the value of the variable resistor may be determined to minimize the amount of the current $I_D$ in the second transistor TN2. For example, the value of the resistor may be determined based on a source voltage $V_{S2}$ of the second transistor TN2, a power supply voltage ($V_{DD}$), and Equation 3 above.

When the first transistor TN1 is turned on and the amount of the gate-to-source voltage $V_{GS,2}$ of the second transistor TN2 is minimized, an amount of the gate-to-source voltage $V_{GS,1}$ of the first transistor TN1 is minimized. Thus, when the first transistor TN1 is changed from an on-state to an off-state, an amount of charges of charge injection, in which channel charges are discharged to the drain D1 and the source S1 of the first transistor TN1, is reduced. As a result, noise generated by the charges of charge injection, is reduced.

Figure 4A:
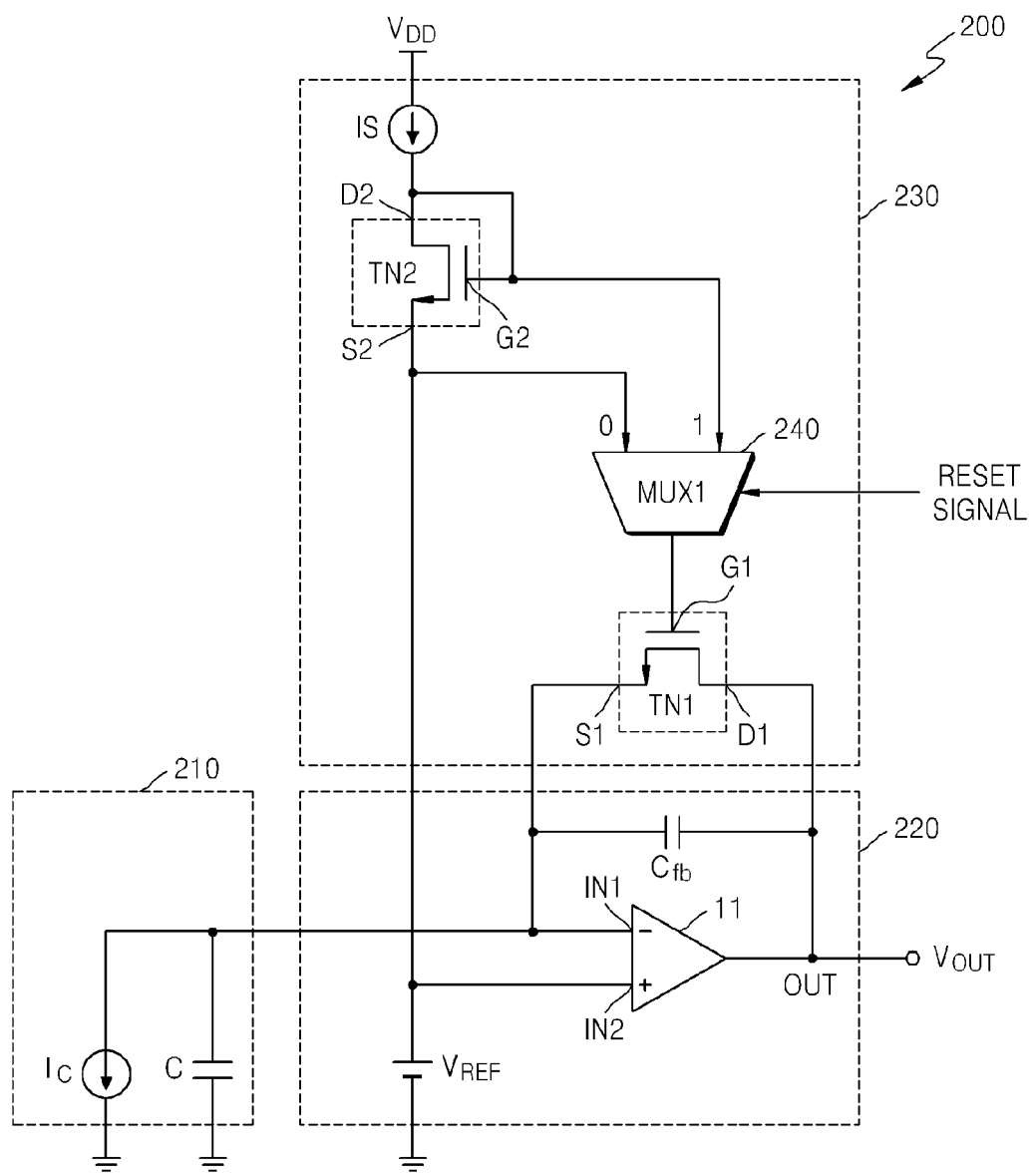
FIGS. 4A through 4D are structural diagrams illustrating examples of charge sense amplifiers.

FIGS. 4A through 4D are structural diagrams illustrating other examples of the charge sense amplifier 200. Referring to FIG. 4A, the sensor 210 includes a current source and a cutoff capacitor C, and the amplifier 220 includes an operation amplifier (OP-AMP) 11 and a feedback capacitor $C_{fb}$. The feedback capacitor $C_{fb}$ is connected between an inverting input terminal IN1 and the output terminal OUT of the OP-AMP 11. The OP-AMP 11 receives a current $I_C$ generated based on charges sensed by the sensor 210, via the inverting input terminal IN1. A voltage $V_{REF}$ corresponding to an initial value of a voltage of the output terminal OUT of the OP-AMP 11 is applied to a non-inverting input terminal IN2 of the OP-AMP 11. The OP-AMP 11 amplifies a voltage difference between the inverting input terminal IN1 and the non-inverting input terminal IN2, and outputs the voltage $V_{OUT}$ via the output terminal OUT. The current $I_C$ of the inverting input terminal IN1 accumulates in the feedback capacitor $C_{fb}$ rather than being input into the OP-AMP 11 due to a relatively high resistance of the inverting input terminal IN1.

The switching circuit 230 includes the first transistor TN1, the second transistor TN2, and the multiplexer 240. The switching circuit 230 shown in FIG. 4A is the same as in FIG. 3, and thus, the detailed description thereof will be omitted. As shown in FIG. 4A, the first transistor TN1 and the second transistor TN2 are N-channel FETs or N-channel MOSFETs. The first transistor TN1 and the second transistor TN2 are the same channel FETs to stably switch on-off the first transistor TN1 by obtaining similar operational properties as a current mirror when the gate voltage $V_{G2}$ of the second transistor TN2 is applied to the gate G1 of the first transistor TN1.

A voltage V(t) applied between two terminals of the feedback capacitor $C_{fb}$ may be calculated according to Equation 4 below.

$$V(t) = \frac{1}{C}\int_0^t I(\tau)d\tau + V(0) \qquad (4)$$

In this example, C is an electrostatic capacity (F) of the feedback capacitor $C_{fb}$, I(τ) is a current (A) input into the inverting input terminal IN1 of the OP-AMP 11, and V(0) is an initial voltage (V) of the feedback capacitor $C_{fb}$.

The first transistor TN1 is connected between the inverting input terminal IN1 and the output terminal OUT of the OP-AMP 11. During a turn-on operation of the first transistor TN1, charges stored in the feedback capacitor $C_{fb}$ are discharged. The source S2 of the second transistor TN2 is connected to the non-inverting input terminal IN2 of the OP-AMP 11. The source S2 and the gate G2, of the second transistor TN2, are connected to input terminals of the multiplexer 240.

In examples, if the reset signal RESET SIGNAL is in a turn-on state to turn on the first transistor TN1, the value of the reset signal RESET SIGNAL may be about 5 V. The reset signal RESET SIGNAL is input into the multiplexer 240, and the multiplexer 240 selects and outputs an input 1 corresponding to the gate voltage $V_{G2}$ of the second transistor TN2. If the reset signal RESET SIGNAL is in a turn-off state to turn off the first transistor TN1, the value of the reset signal RESET SIGNAL may be about 0 V. The reset signal RESET SIGNAL is input into the multiplexer 240, and the multiplexer 240 selects and outputs an input 0 corresponding to the source voltage $V_{S2}$ of the second transistor TN2.

Figure 4B:
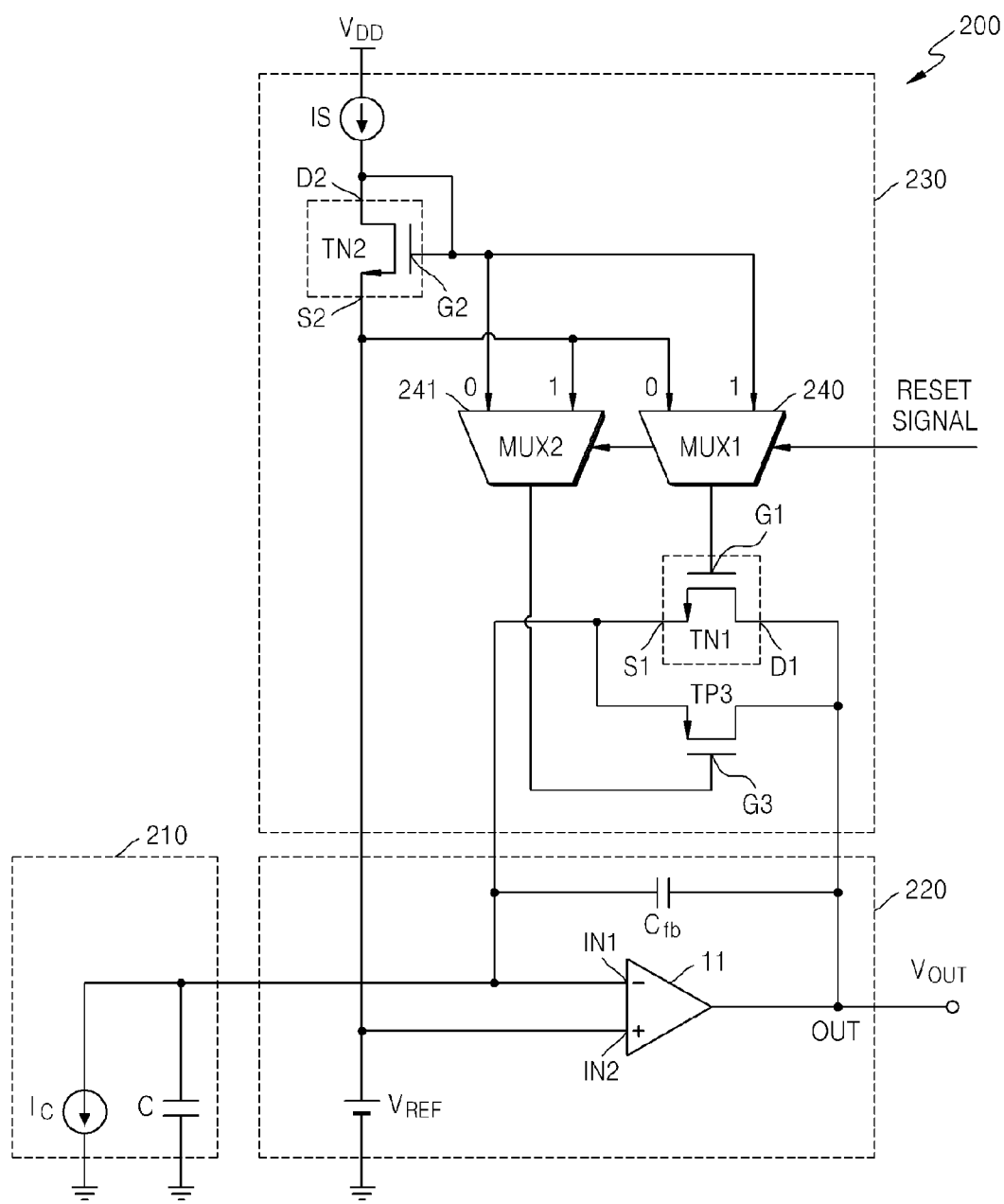

Referring to FIG. 4B, the switching circuit 230 includes the first transistor TN1, the second transistor TN2, a third transistor TP3, the multiplexer 240, and a multiplexer 241. The first transistor TN1, the second transistor TN2, and the multiplexer 240 are the same as in the switching circuit of FIG. 4A, and thus, the detailed description thereof will be omitted. As shown in FIG. 4B, the third transistor TP3 is an P-channel FET or an P-channel MOSFET, and is connected in parallel to the first transistor TN1. In addition, the multiplexer 241 inputs a voltage to a gate G3 of the third transistor TP3. The third transistor TP3 compensates for a negative channel charge generated in the first transistor TN1.

When the reset signal RESET SIGNAL is in a turn-on state to turn on the first transistor TN1 (for example, when the value of the reset signal RESET SIGNAL is about 5 V), and the reset signal RESET SIGNAL is input into the multiplexer 241, the multiplexer 241 selects and outputs an input 1 corresponding to the source voltage $V_{S2}$ of the second transistor TN2. Thus, the source voltage $V_{S2}$ of the second transistor TN2 is input into the gate G3 of the third transistor TP3.

When the reset signal RESET SIGNAL is in a turn-off state to turn off the first transistor TN1 (for example, when the value of the reset signal RESET SIGNAL is about 0 V), and the reset signal RESET SIGNAL is input into the multiplexer 241, the multiplexer 241 selects and outputs an input 0 corresponding to the gate voltage $V_{G2}$ of the second transistor TN2. Thus, the gate voltage $V_{G2}$ of the second transistor TN2 is input into the gate G3 of the third transistor TP3.

Figure 4C:
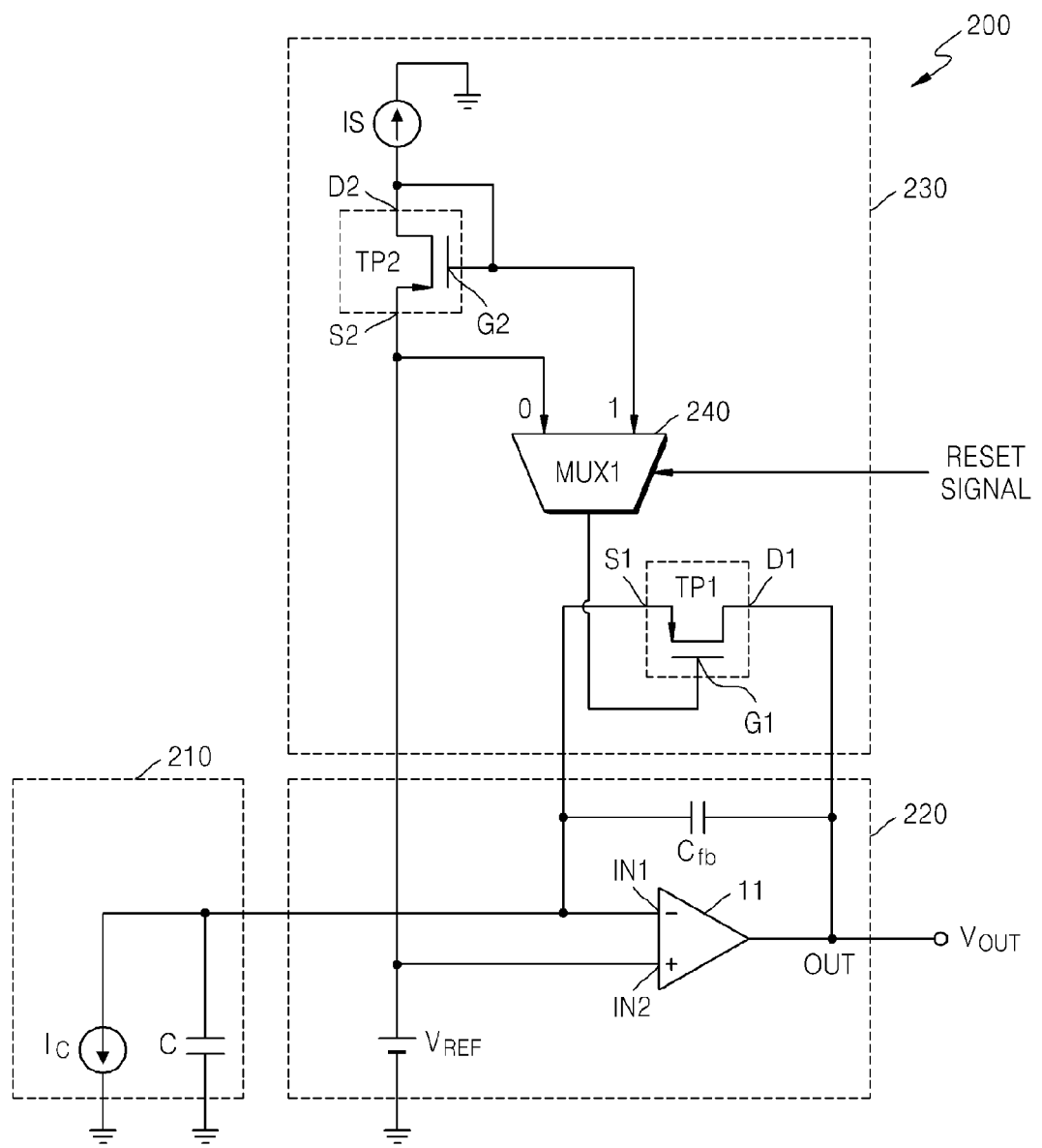

Referring to FIG. 4C, the switching circuit 230 includes a first transistor TP1 and a second transistor TP2 that are P-channel FETs or P-channel MOSFETs. With regard to the second transistor TP2, a current flows from a source S2 to a drain D2 by a current source IS connected to ground. A gate-to-source voltage $V_{GS,2}$ is formed in the second transistor TP2 based on the current between the source S2 and the drain D2 of the second transistor TP2.

When the value of the reset signal RESET SIGNAL is, for example, about 5 V, the multiplexer 240 selects and outputs an input 1 corresponding to a gate voltage $V_{G2}$ of the second transistor TP2. When the value of the reset signal RESET SIGNAL is, for example, about 0 V, the multiplexer 240 selects and outputs an input 0 corresponding to a source voltage $V_{S2}$ of the second transistor TP2. The first transistor TP1 receives the output of the multiplexer 240 via a gate G1 so as to be switched on-off.

Since a source voltage $V_{S1}$ of the first transistor TP1 and the source voltage $V_{S2}$ of the second transistor TP2 are the same, when the gate voltage $V_{G2}$ of the second transistor TP2 is applied to the gate G1 of the first transistor TP1, the first transistor TP1 and the second transistor TP2 operate as a current mirror. Thus, when the gate voltage $V_{G2}$ of the second transistor TP2 is applied to the gate G1 of the first transistor TP1, the same current as the current flowing in the second transistor TP2 flows in the first transistor TP1. In addition, a gate-to-source voltage $V_{GS,2}$ of the second transistor TP2 is the same as a gate-to-source voltage $V_{GS,1}$ of the first transistor TP1, because of the current flowing in the second transistor TP2. Thus, the first transistor TP1 is turned on.

The current source IS is set to minimize an amount of the current flowing in the second transistor TP2. Accordingly, a relatively small amount of current also flows in the first transistor TP1 when the gate voltage $V_{G2}$ of the second transistor TP2 is applied to the gate G1 of the first transistor TP1. Thus, an amount of the gate-to-source voltage $V_{GS,1}$ of the first transistor TP1 is reduced, and an amount of charge injection charges of the first transistor TP1 is reduced. In addition, when the source voltage $V_{S2}$ of the second transistor TP2 is input into the gate G1 of the first transistor TP1, the gate-to-source voltage $V_{GS,1}$ of the first transistor TP1 is about 0 V that is greater than a threshold voltage (for example, about −0.5 V) of the first transistor TP1. Thus, the first transistor TP1 is turned off.

Figure 4D:
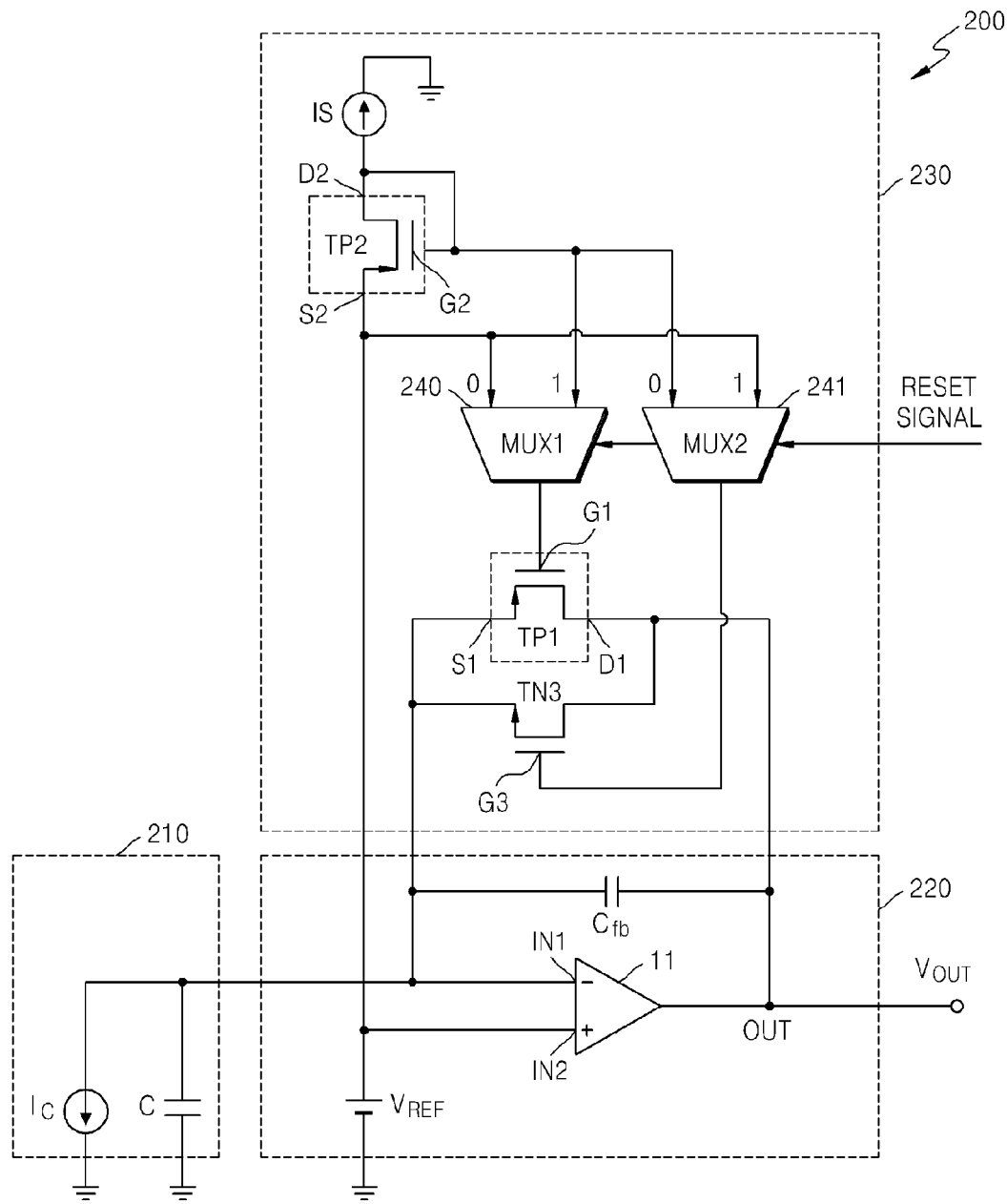

Referring to FIG. 4D, the switching circuit 230 includes the first transistor TP1, the second transistor TP2, a third transistor TN3, and the multiplexers 240 and 241. The first transistor TP1, the second transistor TP2, and the multiplexer 240 are the same as in the switching circuit of FIG. 4C, and thus, the detailed description thereof will be omitted. As shown in FIG. 4D, the third transistor TN3 is an N-channel FET or an N-channel MOSFET, and is connected in parallel to the first transistor TP1. In addition, the multiplexer 241 applies a voltage to a gate G3 of the third transistor TN3. The third transistor TN3 compensates for a positive channel charge generated in the first transistor TP1.

When the reset signal RESET SIGNAL is in a turn-on state to turn on the first transistor TP1, and the reset signal RESET SIGNAL is input into the multiplexer 241, the multiplexer 241 selects and outputs an input 1 corresponding to the source voltage $V_{S2}$ of the second transistor TP2. Thus, the source voltage $V_{S2}$ of the second transistor TP2 is applied to the gate G3 of the third transistor TN3.

When the reset signal RESET SIGNAL is in a turn-off state to turn off the first transistor TP1, and the reset signal RESET SIGNAL is input into the multiplexer 241, the multiplexer 241 selects and outputs an input 0 corresponding to the gate voltage $V_{G2}$ of the second transistor TP2. Thus, the gate voltage $V_{G2}$ is input into the gate G3 of the third transistor TN3.

Figure 5:
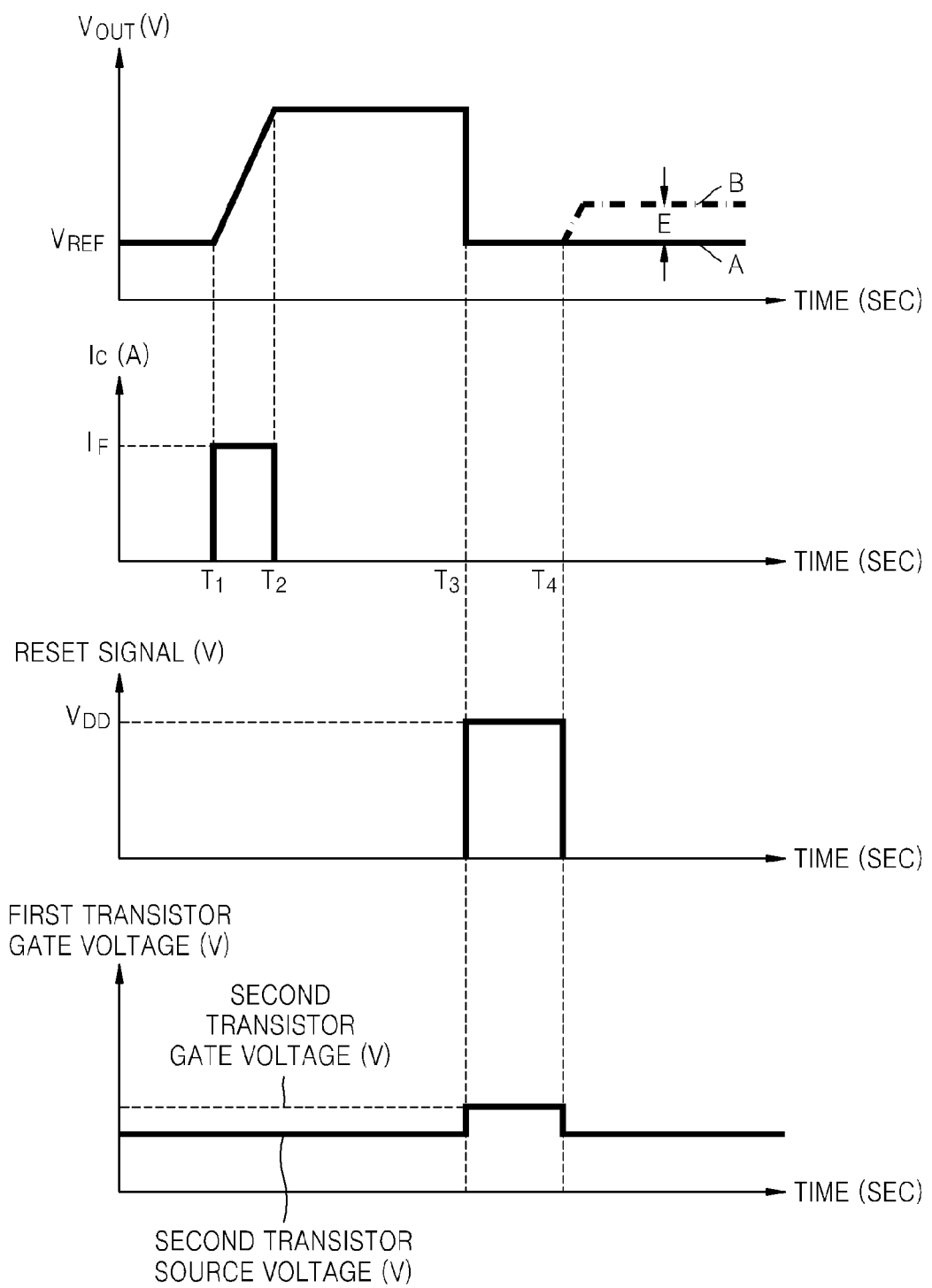
FIG. 5 is a graph illustrating examples of waveforms of a voltage of an output terminal of an operation amplifier (OP-AMP), a current of an input terminal of the OP-AMP, a reset signal, and a gate voltage of a first transistor, of the charge sense amplifier of FIG. 4A.

FIG. 5 is a graph illustrating examples of waveforms of the voltage $V_{OUT}$ of the output terminal OUT of the OP-AMP 11, the current $I_c$ of the inverting input terminal IN1 of the OP-AMP 11, the reset signal RESET SIGNAL, and a gate voltage $V_{G1}$ of the first transistor TN1, of the charge sense amplifier 200 of FIG. 4A. Within a period of time 0 to T1 when a current pulse $I_F$ is not input, the voltage $V_{OUT}$ is maintained at the initial value $V_{REF}$. Within a period of time T1 to T2 when the current pulse $I_F$ is input into the inverting input terminal IN1, charges accumulate in the feedback capacitor $C_{fb}$, and thus, the voltage $V_{OUT}$ is amplified and output to the output terminal OUT.

Within a period of time T2 to T3 after the current pulse $I_F$ is input, the voltage $V_{OUT}$ of the output terminal OUT of the OP-AMP 11 is measured. Within a period of time T3 to T4, a power supply voltage $V_{DD}$ used in a semiconductor integrated circuit is input as the reset signal RESET SIGNAL into the multiplexer 240, to sense a next current pulse $I_F$. Accordingly, the gate voltage $V_{G2}$ of the second transistor TN2, instead of the source voltage $V_{S2}$ of the second transistor TN2, is applied as the gate voltage $V_{G1}$ of the first transistor TN1. As such, the first transistor TN1 is turned on, a short circuit occurs between the two terminals of the feedback capacitor $C_{fb}$, and a reset operation of discharging charges stored in the feedback capacitor $C_{fb}$, is performed.

In the switching circuit 230 shown in FIG. 4A, since a source voltage $V_{S1}$ of the first transistor TN1 is the same as the source voltage $V_{S2}$ of the second transistor TN2 when the gate voltage $V_{G2}$ of the second transistor TN2 is applied to the gate G1 of the first transistor TN1, the gate-to-source voltage $V_{GS,1}$ of the first transistor TN1 is the same as the gate-to-source voltage $V_{GS,2}$ of the second transistor TN2. Thus, the first transistor TN1 and the second transistor TN2 function as a current mirror. A current flowing into the second transistor TN2 due to the current source IS also flows into the first transistor TN1 when the gate voltage $V_{G2}$ of the second transistor TN2 is applied to the gate G1 of the first transistor TN1. Therefore the first transistor TN1 is turned on.

Referring to FIG. 5, if the switching operation of the first transistor TN1 is performed by applying the reset signal RESET SIGNAL directly to the gate G1 of the first transistor TN1, an offset voltage of the OP-AMP 11 may be temporarily generated due to the charge injection of the first transistor TN1. In addition, since the offset voltage is amplified by the OP-AMP 11, the voltage $V_{OUT}$ of the output terminal OUT of the OP-AMP 11 may cause noise E rather than being reset to the initial value $V_{REF}$, as shown in B of FIG. 5. On the other hand, in examples, an amount of the gate-to-source voltage $V_{GS,1}$ of the first transistor TN1 is minimized when the first transistor TN1 is turned on, and thus, an amount of charge injection charges discharged from channels of the first transistor TN1 is reduced. Accordingly, as shown in 'A' of FIG. 5, the voltage $V_{OUT}$ is accurately reset to the initial value $V_{REF}$ without noise, and thus, an accuracy of sensing of the charge sense amplifier 200 is increased.

Figure 6:
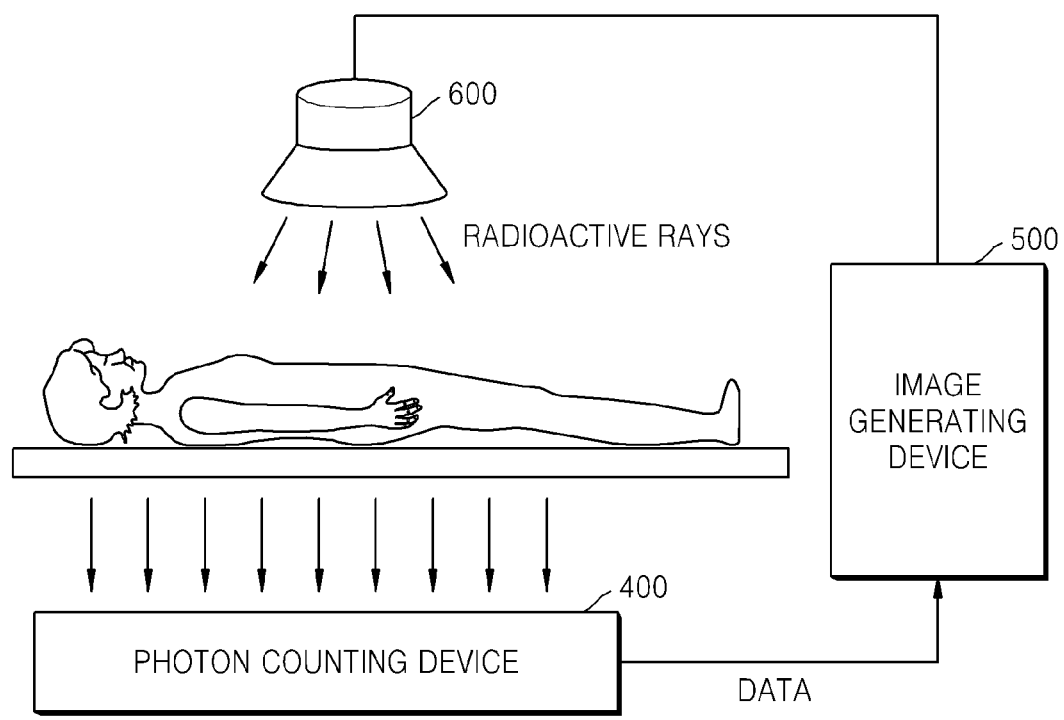
FIG. 6 is a diagram illustrating an example of a medical image system using radioactive rays.

FIG. 6 is a structural diagram illustrating an example of a medical image system using radioactive rays. The medical image system includes a radiation generating device 600, a photon counting device 400, and an image generating device 500. The radiation generating device 600 generates the radioactive rays and irradiates the radioactive rays to a subject, such as a human body of a patient. Examples of the radioactive rays include various rays, such as supersonic rays, alpha rays, beta rays, gamma rays, X-rays, and/or neutron rays. The photon counting device 400 detects the radioactive rays transmitted through the human body using a sensor, and counts photons included in the detected radioactive rays. The image generating device 500 generates a radioactive image to distinguish human anatomies based on data (e.g., the counted photons) output from the photon counting device 400.

Figure 7:
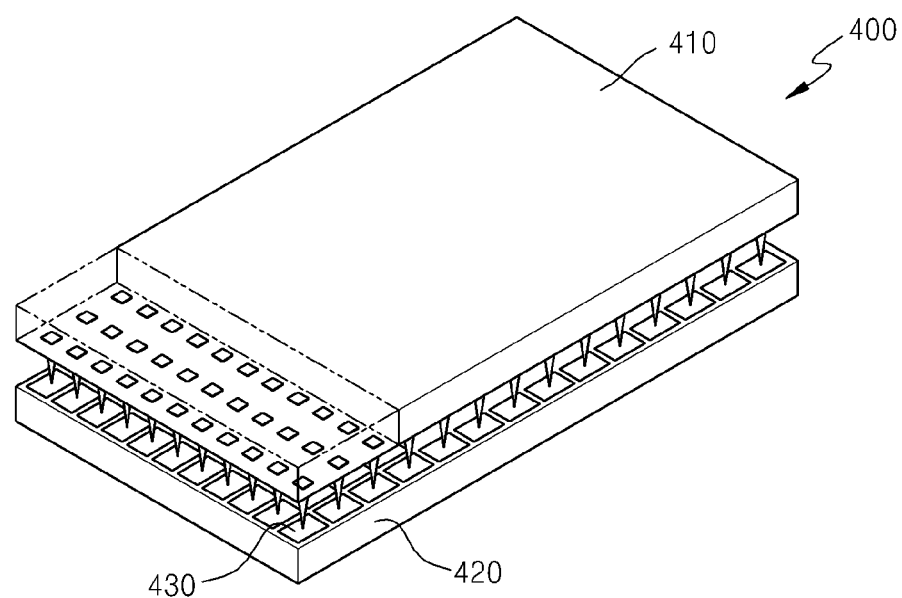
FIG. 7 is a perspective view illustrating an example of a photon counting device.

FIG. 7 is a perspective view illustrating an example of the photon counting device 400. The photon counting device 400 includes a sensor 410 and a read chip 420. The sensor 410 corresponds to a photographing region of the subject to be photographed, and includes unit sensors corresponding to sub regions of the sensor 410, which respectively correspond to pixels of the photographing region. Each of the unit sensors detects the photons included in the radioactive rays incident thereon, and converts the photons into electrical signals corresponding to a number of the photons. The read chip 420 includes read circuits 430 respectively corresponding to the pixels of the photographing region. Each unit sensor outputs the respective electrical signal to each of the read circuits 430 corresponding to a region where the photons are detected, through a unit output terminal corresponding to each unit sensor.

Figure 8:
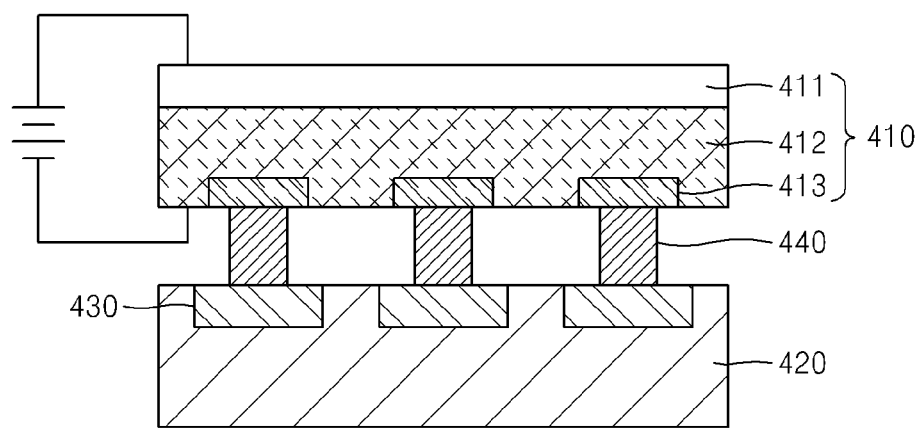
FIG. 8 is a cross-sectional view illustrating an example of the photon counting device.

FIG. 8 is a cross-sectional view illustrating an example of the photon counting device 400. The sensor 410 generates an electron-hole pair when photons are incident on a depletion region 412. The electron-hole pair is attracted to an N-type neutral region 411 and a P-type neutral region 413 under the influence of an electric field and flows outwards. The sensor 410 includes, but is not limited to, the N-type neutral region 411, the depletion region 412, and the P-type neutral region 413. It will be understood by one of ordinary skill in the art that various sensors configured to detect photons may be used. The unit sensors of the sensor 410 detects photons, converts the photons into electrical signals, and respectively outputs the converted electrical signals to the read circuits 430 of the read chip 420 through bondings 440. That is, the unit sensors and the read circuits 430 are connected to each other through the bonding 440. Alternatively, the unit sensors and the read circuits 430 may be connected to each other by forming the sensor 410 on the read chip 420 via a vapor deposition method. It will be understood by one of ordinary skill in the art that this example is not limited to the bonding method and the vapor deposition method.

The read chip 420 may include a 2-dimensional pixel array (2-D pixel array) including the read circuits 430 respectively corresponding to the unit sensors of the sensor 410. Each read circuit 430 counts the photons based on the electrical signal converted from the photons and received from the sensor 410. Each read circuit 430 outputs the count data to the image generating device 500 of FIG. 6. Examples of a method of reading the electrical signal received from each unit sensor in each read circuit 430 may include a charge integration mode and/or a photon counting mode. The charge integration mode is a method of accumulating the electrical signals generated for a predetermined period of time in a charge integration capacitor so as to read the electrical signals via an analog/digital (A/D) converter. The photon counting mode is a method of comparing an electrical signal input from each unit sensor with a predetermined threshold value so as to output a digital signal '1' or '0', and counting existences of the digital signal '1' via a counter so as to output the result in a digital form. In the photon counting mode, whenever the electrical signals are generated by a single unit sensor, the electrical signals are compared with a predetermined threshold value via a comparer, and are counted.

Figure 9:
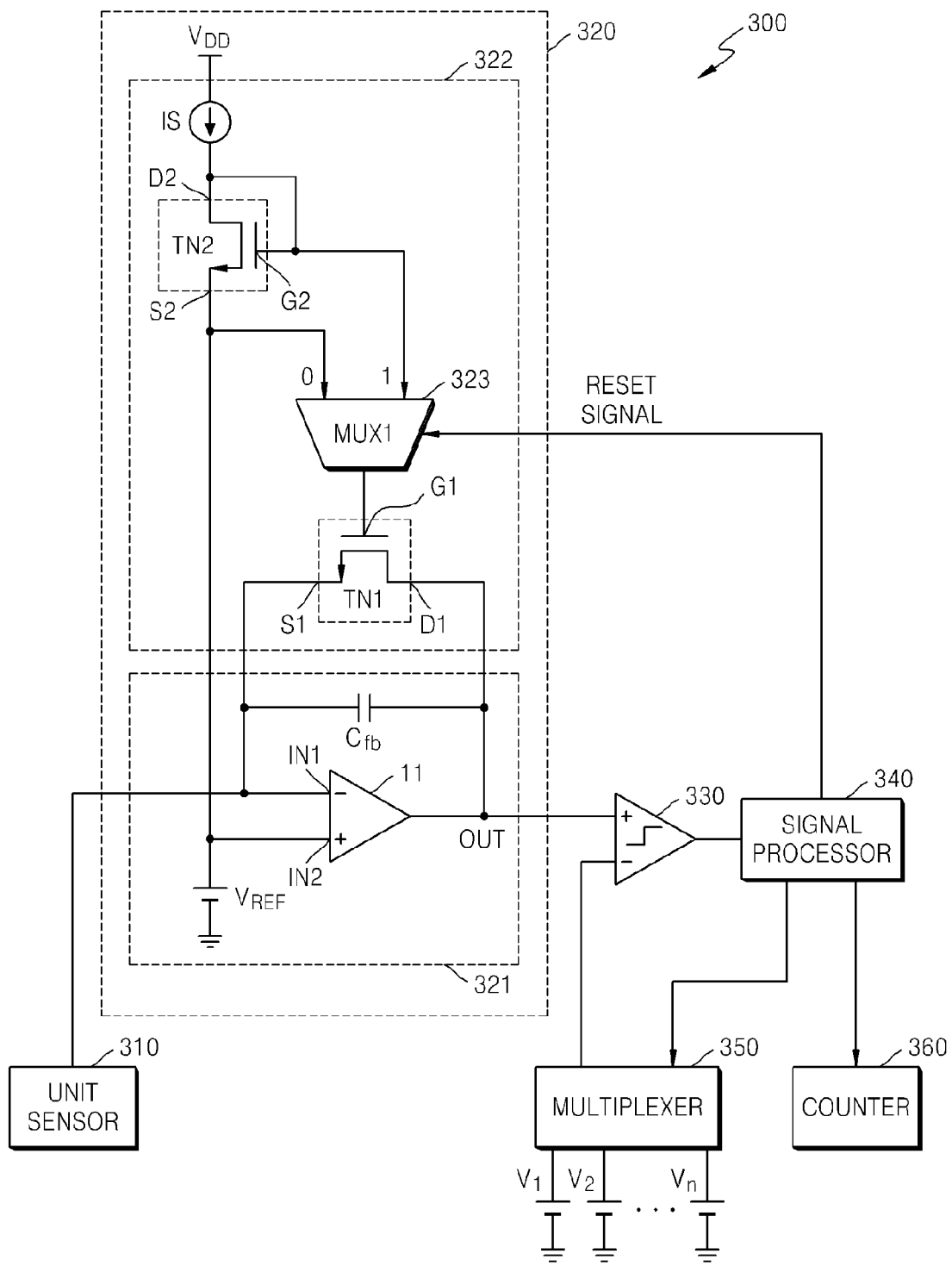
FIG. 9 is a structural diagram illustrating an example of a read circuit of a photon counting device.

FIG. 9 is a structural diagram of a read circuit 300 of a photon counting device. With reference to FIG. 9, the photon counting device including the read circuit 300 using a photon counting mode, will be described. The read circuit 300 includes a charge detecting amplifier 320 including an amplifier 321 and a switching circuit 322. The read circuit 300 further includes a comparer 330, a signal processor 340, a multiplexer 350, and a counter 360.

The amplifier 321 receives electrical signals from a unit sensor 310, accumulates the electrical signals in a feedback capacitor $C_{fb}$, and outputs an accumulated voltage of the output terminal OUT to the comparer 330. The amplifier 321 accumulates the electrical signals received from the unit sensor 310 until the signal processor 340 transmits a reset signal RESET SIGNAL to turn on the first transistor TN1. When the signal processor 340 outputs the reset signal RESET SIGNAL to the switching circuit 322, the voltage of the output terminal OUT of the amplifier 321 is restored to an initial value $V_{REF}$ prior to accumulating the electrical signals. The amplifier 321 maintains the accumulated voltage in the output terminal OUT until a reset command is issued, and outputs the accumulated voltage in the output terminal OUT to the comparer 330.

The comparer 330 compares the voltage accumulated by the amplifier 321 with at least one threshold value V1, V2, and/or Vn received from the multiplexer 350, and outputs the comparison result to the signal processor 340. The threshold values V1, V2, and Vn refer to predetermined amplitudes of voltages to distinguish an energy band of photons included in radioactive rays into at least two portions. If the comparer 330 determines that the voltage of the output terminal OUT is greater than the threshold voltage, the signal processor 340 orders the multiplexer 350 to output, to the comparer 330, a new threshold voltage that is higher than the current threshold voltage.

If the comparer 330 determines that the voltage of the output terminal OUT is smaller than the threshold voltage, the signal processor 340 orders the multiplexer 350 to output, to the comparer 330, a new threshold voltage that is lower than the current threshold voltage. Thus, the comparer 330 compares the voltage in the output terminal OUT of the amplifier 321 with the new threshold voltage input from the multiplexer 350, and outputs the comparison result to the signal processor 340. By repeating these processes, the voltage of the output terminal OUT of the amplifier 321 is accurately detected by comparing the voltage in the output terminal OUT of the amplifier 321 with various threshold voltages V1 through Vn provided from the multiplexer 350.

The signal processor 340 receives, from the comparer, the threshold voltage and the voltage of the output terminal OUT, and outputs, to the counter 360, a digital signal to distinguish the energy band of the photons included in the radioactive rays. In addition, when the voltage in the output terminal OUT is detected, the signal processor 340 transmits the reset signal RESET SIGNAL to request to reset the amplifier 321 to the initial value in order to detect a new voltage of the output terminal OUT of the amplifier 321 due to next input photons. The reset signal RESET SIGNAL is transmitted to a multiplexer 323 of the switching circuit 322. The multiplexer 323 selects a gate voltage or a source voltage of a second transistor TN2 based on the reset signal RESET SIGNAL received from the signal processor 340, and inputs the selected voltage to a gate G1 of a first transistor TN1 to turn on-off the first transistor TN1.

The counter 360 distinguishes and counts the photons of various energy bands based on the digital signal received from the signal processor 340. That is, the counter 360 counts an accumulating number of photons for each energy band based on the received digital signal. The counter 360 may include a circuit configured to count the accumulating number of photons using an input as a predetermined clock in a predetermined order. The detailed description about the amplifier 220 and the switching circuit 230 of the charge sense amplifier 200 of FIG. 4A is also applied respectively to the amplifier 321 and the switching circuit 322 of FIG. 9.

The photon counting device reduces an amount of charge injection charges discharged from channels of a transistor (e.g., the first transistor TN1) in a reset operation of the charge detecting amplifier 320, thereby reducing noise. Thus, whenever the photons are detected, properties of the charge detecting amplifier 320 are maintained constant, and thus, a high-quality X-ray digital image is generated.

When the read circuits 430 of FIGS. 7-8 are embodied by using a single semiconductor wafer, a threshold voltage property of a transistor included in each read circuit 430 may vary based on a position of the semiconductor wafer. However, the photon counting device 400 allows a relatively small amount of current to flow in a transistor included in each read circuit 430, and thus, performs a switching operation of the transistor using a gate-to-source voltage of the transistor. Therefore, the switching operation of the transistor is ensured while reducing the amount of charge injection charges to reduce noise.

According to the teachings above, there is provided a transistor, which may reduce an amount of charge injection during a switching on-off operation of the transistor. In addition, during a reset operation of a charge sense amplifier, noise due to charge injection may be reduced, and thereby, detection accuracy of the charge sense amplifier and a photon counting device, may be increased.

It should be understood that the examples described herein should be considered in a descriptive sense only and not for purposes of limitation. Descriptions of features or aspects within each example should typically be considered as available for other similar features or aspects in other examples.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A switching circuit configured to close and open a connection between a first terminal and a second terminal of a predetermined circuit element, comprising:
  a first transistor comprising a source connected to the first terminal, a drain connected to the second terminal, and a gate;
  a second transistor comprising a drain, a source, and a gate connected to the drain of the second transistor;

a current source configured to supply a current flowing through the drain and the source of the second transistor, to generate a gate voltage of the gate of the second transistor; and a multiplexer configured to
receive the gate voltage, a reference voltage, and a control signal, and
selectively apply the gate voltage or the reference voltage to the gate of the first transistor based on the control signal.

2. The switching circuit of claim 1, wherein the reference voltage is a source voltage of the source of the second transistor.

3. The switching circuit of claim 1, wherein:
the first transistor and the second transistor are N-channel field effect transistors (FETs); and
a source voltage of the source of the second transistor is equal to or greater than a voltage of the first terminal.

4. The switching circuit of claim 1, wherein:
the first transistor and the second transistor are P-channel FETs; and
a source voltage of the source of the second transistor is equal to or less than a voltage of the first terminal.

5. The switching circuit of claim 1, wherein:
the first transistor and the second transistor are N-channel FETs; and
the reference voltage is equal to or less than the voltage of the first terminal.

6. The switching circuit of claim 1, wherein:
the first transistor and the second transistor are P-channel FETs; and
the reference voltage is equal to or greater than the voltage of the first terminal.

7. The switching circuit of claim 1, wherein the source of the second transistor is connected to the first terminal.

8. The switching circuit of claim 1, wherein the multiplexer is further configured to:
apply the gate voltage to the gate of the first transistor when the control signal is in a turn-on state to turn on the first transistor; and
apply reference voltage when the control signal is in a turn-off state to turn off the first transistor.

9. The switching circuit of claim 1, further comprising:
a third transistor comprising a source connected to the first terminal, a drain connected to the second terminal, and a gate; and
another multiplexer configured to
receive the gate voltage, the reference voltage, and the control signal, and
selectively apply the gate voltage or the reference voltage to the gate of the third transistor based on the control signal.

10. The switching circuit of claim 9, wherein:
the first transistor and the second transistor are N-channel FETs; and
the third transistor is an P-channel field effect transistor (FET).

11. The switching circuit of claim 9, wherein:
the first transistor and the second transistor are P-channel FETs; and
the third transistor is an N-channel FET.

12. The switching circuit of claim 9, wherein the other multiplexer is further configured to:

apply the reference voltage to the gate of the third transistor when the control signal is in a turn-on state to turn on the first transistor; and
apply the gate voltage to the gate of the third transistor when the control signal is in a turn-off state to turn off the first transistor.

13. The switching circuit of claim 1, wherein the current from the current source is a minimum current to turn on the second transistor.

14. A charge sense amplifier comprising:
an amplifier comprising an input terminal and an output terminal, and configured to
receive a signal from the input terminal,
amplify the signal, and
output the amplified signal to the output terminal; and
a switching circuit configured to reset the amplifier to output an initial-valued signal based on a reset signal, the switching circuit comprising
a first transistor comprising a source connected to the input terminal, a drain connected to the output terminal, and a gate,
a second transistor comprising a drain, a source, and a gate connected to the drain of the second transistor,
a current source configured to supply a current flowing through the drain and the source of the second transistor, to generate a gate voltage of the gate of the second transistor, and
a multiplexer configured to
receive the gate voltage, a reference voltage, and the reset signal, and
selectively apply the gate voltage or the reference voltage to the gate of the first transistor based on the reset signal.

15. The charge sense amplifier of claim 14, wherein the reference voltage is a source voltage of the source of the second transistor.

16. The charge sense amplifier of claim 14, wherein:
the first transistor and the second transistor are N-channel FETs; and
the reference voltage is equal to or less than a voltage of the input terminal.

17. The charge sense amplifier of claim 14, wherein:
the first transistor and the second transistor are P-channel FETs; and
the reference voltage is equal to or greater than a voltage of the input terminal.

18. The charge sense amplifier of claim 14, wherein:
the input terminal comprises an inverting input terminal and a non-inverting input terminal;
the source of the second transistor is connected to the non-inverting input terminal; and
the multiplexer is further configured to
apply the gate voltage to the gate of the first transistor when the reset signal is in a turn-on state to turn on the first transistor, and
apply the reference voltage to the gate of the first transistor when the reset signal is in a turn-off state to turn off the first transistor.

19. The charge sense amplifier of claim 14, further comprising:
a third transistor comprising a source connected to the input terminal, a drain connected to the output terminal, and a gate; and
another multiplexer configured to:
receive the gate voltage, the reference voltage, and the reset signal, and selectively apply the gate voltage or the reference voltage to the gate of the third transistor based on the reset signal.

20. The charge sense amplifier of claim 19, wherein:
the first transistor and the second transistor are N-channel FETs; and
the third transistor is an P-channel field effect transistor (FET).

21. The charge sense amplifier of claim 19, wherein:
the first transistor and the second transistor are P-channel FETs; and
the third transistor is an N-channel FET.

22. The charge sense amplifier of claim 19, wherein the other multiplexer is further configured to:
apply the reference voltage to the gate of the third transistor when the reset signal is in a turn-on state to turn on the first transistor; and
apply the gate voltage to the gate of the third transistor when the reset signal is in a turn-off state to turn off the first transistor.

23. The charge sense amplifier of claim 14, wherein the current source is set to minimize the current.

24. A photon counting device comprising:
a sensor unit comprising unit sensors configured to
detect photons of radioactive rays, and
convert the photons into an signal; and
a read chip comprising read circuits respectively corresponding to the unit sensors,
wherein each of the read circuits comprises
an amplifier comprising an input terminal and an output terminal, and configured to
receive the signal from a corresponding one of the unit sensors,
amplify the signal, and
output the amplified signal to the output terminal,
a switching circuit configured to reset the amplifier to output an initial-valued signal based on a reset signal,
a comparer configured to
compare a voltage of the output terminal with a predetermined threshold value, and
output a result of the comparison,
a signal processor configured to
receive the result of the comparison from the comparer, and
transmit the reset signal to the switching circuit and a digital signal based on the result of the comparison, and a counter configured to
receive the digital signal from the signal processor, and
count a number of photons based on the digital signal, and
wherein the switching circuit comprises
a first transistor comprising a source connected to the input terminal, a drain connected to the output terminal, and a gate,
a second transistor comprising a drain, a source, and a gate connected to the drain of the second transistor,
a current source configured to supply a current flowing through the drain and the source of the second transistor, to generate a gate voltage of the gate of the second transistor, and
a multiplexer configured to
receive the gate voltage, a reference voltage, and the reset signal, and
selectively apply the gate voltage or the reference voltage to the gate of the first transistor based on the reset signal.

25. The photon counting device of claim 24, wherein:
the source of the second transistor is connected to the input terminal;
the reference voltage is a source voltage of the source of the second transistor; and
the multiplexer is further configured to
apply the gate voltage to the gate of the first transistor when the reset signal is in a turn-on state to turn on the first transistor, and
apply the reference voltage to the gate of the first transistor when the reset signal is in a turn-off state to turn off the first transistor.

26. An apparatus comprising:
a circuit element comprising a first terminal and a second terminal;
a first transistor configured to close and open a connection between the first terminal and the second terminal;
a second transistor comprising a drain connected to a current source, a source, and a gate connected to the drain of the second transistor, the second transistor configured to generate a voltage of the gate and a voltage of the source; and
a multiplexer configured to
receive the voltage of the gate, the voltage of the source, and a control signal, and
turn on and off the first transistor based on the voltage of the gate, the voltage of the source, and the control signal, to close and open the connection.

* * * * *